United States Patent
Uematsu et al.

(10) Patent No.: US 10,793,821 B2
(45) Date of Patent: Oct. 6, 2020

(54) TEST DEVICE

(71) Applicant: HITACHI HIGH-TECHNOLOGIES CORPORATION, Tokyo (JP)

(72) Inventors: Chihiro Uematsu, Tokyo (JP); Muneo Maeshima, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 5 days.

(21) Appl. No.: 15/544,302

(22) PCT Filed: Jan. 22, 2016

(86) PCT No.: PCT/JP2016/051770
§ 371 (c)(1),
(2) Date: Jul. 18, 2017

(87) PCT Pub. No.: WO2016/121627
PCT Pub. Date: Aug. 4, 2016

(65) Prior Publication Data
US 2018/0010084 A1 Jan. 11, 2018

(30) Foreign Application Priority Data
Jan. 27, 2015 (JP) ................................. 2015-013445

(51) Int. Cl.
*C12M 1/34* (2006.01)
*C12M 1/32* (2006.01)
(Continued)

(52) U.S. Cl.
CPC .............. *C12M 41/36* (2013.01); *C12M 1/34* (2013.01); *C12M 23/12* (2013.01); *C12M 41/46* (2013.01);
(Continued)

(58) Field of Classification Search
CPC .......... A63B 2071/088; A63B 2208/12; A63B 71/085; C12M 1/34; C12M 23/12;
(Continued)

(56) References Cited

U.S. PATENT DOCUMENTS
5,698,414 A 12/1997 Ollar
2002/0128578 A1 9/2002 Johnson et al.
(Continued)

FOREIGN PATENT DOCUMENTS
EP 2757371 A1 7/2014
JP 04-346779 A 12/1992
(Continued)

OTHER PUBLICATIONS

Extended European Search Report dated Jul. 6, 2018 for the European Patent Application No. 16743230.1.
(Continued)

*Primary Examiner* — Gautam Prakash
*Assistant Examiner* — Lydia Edwards
(74) *Attorney, Agent, or Firm* — Volpe and Koenig, P.C.

(57) ABSTRACT

The invention provides a technology for promptly determining bacterial identification or an antimicrobial susceptibility testing. In the invention, first, a state where the bacteria are divided is monitored by performing microscopic observation with respect to the shape or the number of bacteria in each of wells of a culture plate for bacterial identification culture or the antimicrobial susceptibility testing. In addition, the shape, the number or the area of the bacteria are interpreted from the image obtained by the microscopic observation whether or not the bacteria proliferate at a stage from an induction phase to a logarithmic phase, and the time-dependent changes thereof are made into a graph. From the graph, it is determined whether or not the bacteria proliferate for each measurement, the determination results are displayed on the screen, and accordingly, the result of the antimicrobial susceptibility is provided every time when the measurement is performed (FIG. 12).

15 Claims, 17 Drawing Sheets

(51) Int. Cl.
*C12Q 1/08* (2006.01)
*G02B 21/26* (2006.01)
*G06T 7/00* (2017.01)
*G06T 1/00* (2006.01)
*C12Q 1/04* (2006.01)
*G02B 21/36* (2006.01)

(52) U.S. Cl.
CPC .................. *C12Q 1/04* (2013.01); *C12Q 1/08* (2013.01); *G06T 1/00* (2013.01); *G06T 7/0016* (2013.01); *G02B 21/26* (2013.01); *G02B 21/367* (2013.01); *G02B 21/368* (2013.01); *G06T 2207/10056* (2013.01)

(58) Field of Classification Search
CPC ......... C12M 41/36; C12M 41/46; C12Q 1/04; C12Q 1/08; G02B 21/26; G02B 21/367; G02B 21/368; G06T 1/00; G06T 2207/10056; G06T 7/0016
See application file for complete search history.

(56) References Cited

U.S. PATENT DOCUMENTS

| | | |
|---|---|---|
| 2002/0155515 A1 | 10/2002 | Farina et al. |
| 2005/0095665 A1 | 5/2005 | Williams et al. |
| 2006/0265173 A1* | 11/2006 | Mishima ............... G01N 15/147 702/118 |
| 2014/0349333 A1 | 11/2014 | Matsumoto et al. |
| 2017/0096631 A1 | 4/2017 | Uematsu et al. |

FOREIGN PATENT DOCUMENTS

| | | |
|---|---|---|
| JP | 08-511676 A | 12/1996 |
| JP | 2002-543434 A | 12/2002 |
| JP | 2004-520593 A | 7/2004 |
| JP | 2005-261260 A | 9/2005 |
| JP | 2010-213598 A | 9/2010 |
| WO | 93/21511 A1 | 10/1993 |
| WO | 1997/012957 A1 | 4/1997 |
| WO | 1999/006589 A1 | 2/1999 |
| WO | 2000/067037 A2 | 11/2000 |
| WO | 01/09371 A1 | 2/2001 |
| WO | 2002/086054 A1 | 10/2002 |
| WO | 2013/038925 A1 | 3/2013 |
| WO | 2014/145899 A1 | 9/2014 |
| WO | 2015/141040 A1 | 9/2015 |

OTHER PUBLICATIONS

Journal of Clinical Microbiology, 2000, vol. 38, No. 6, p. 2108-2111.
Japanese Journal of Chemotherapy, 2002, vol. 50, No. 5, p. 259-265.
International Search Report for WO 2016/121627 A1, dated Apr. 5, 2016.

* cited by examiner

[Fig. 1]
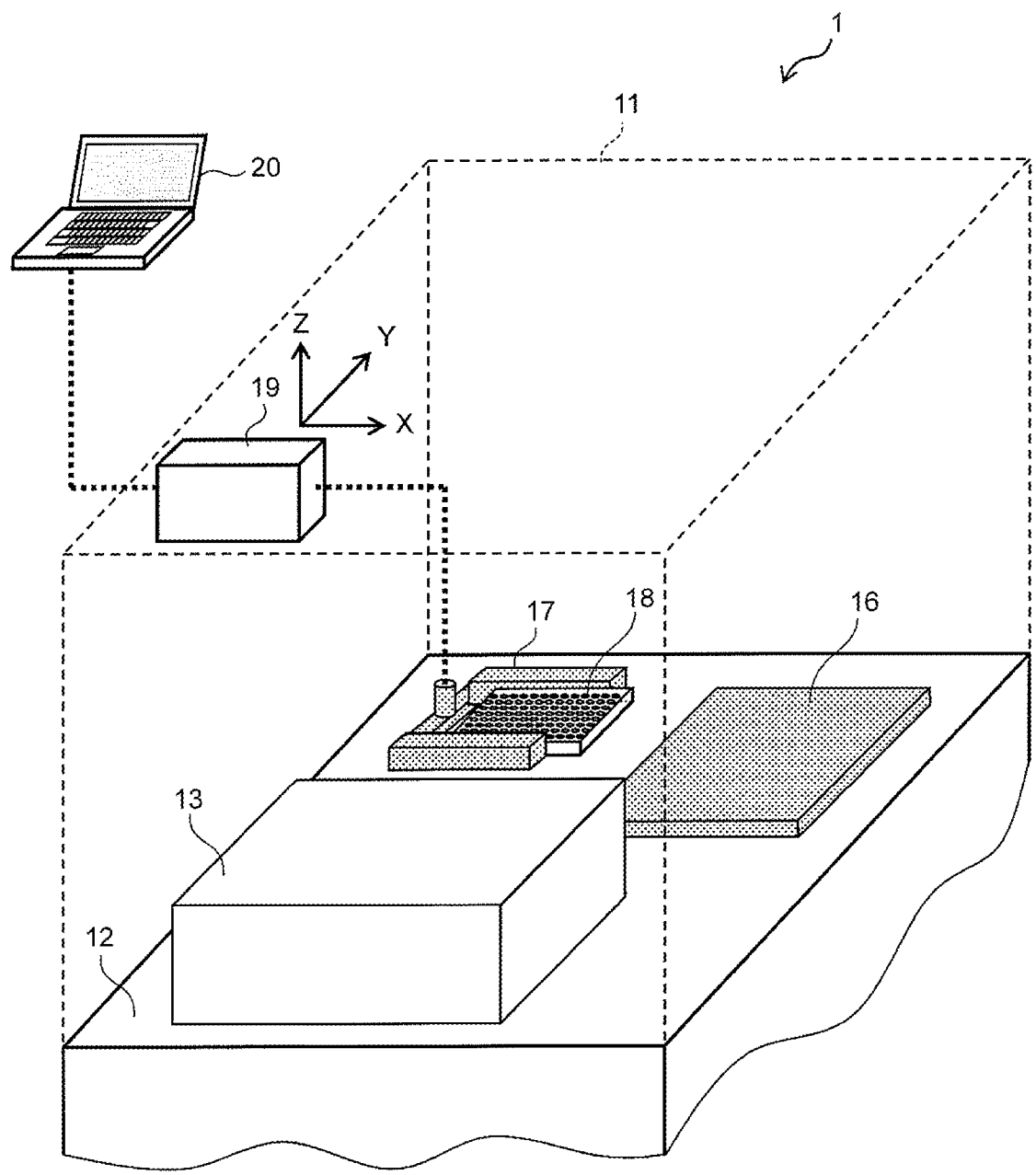

[Fig. 2]
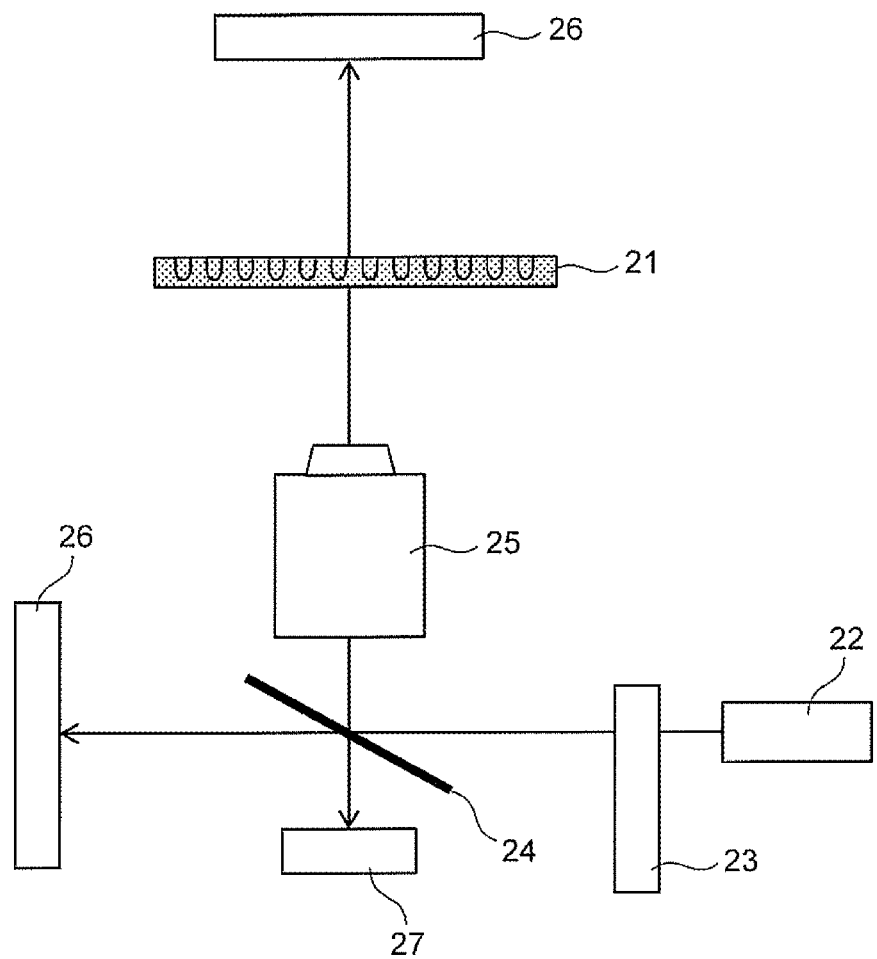

[Fig. 3A]
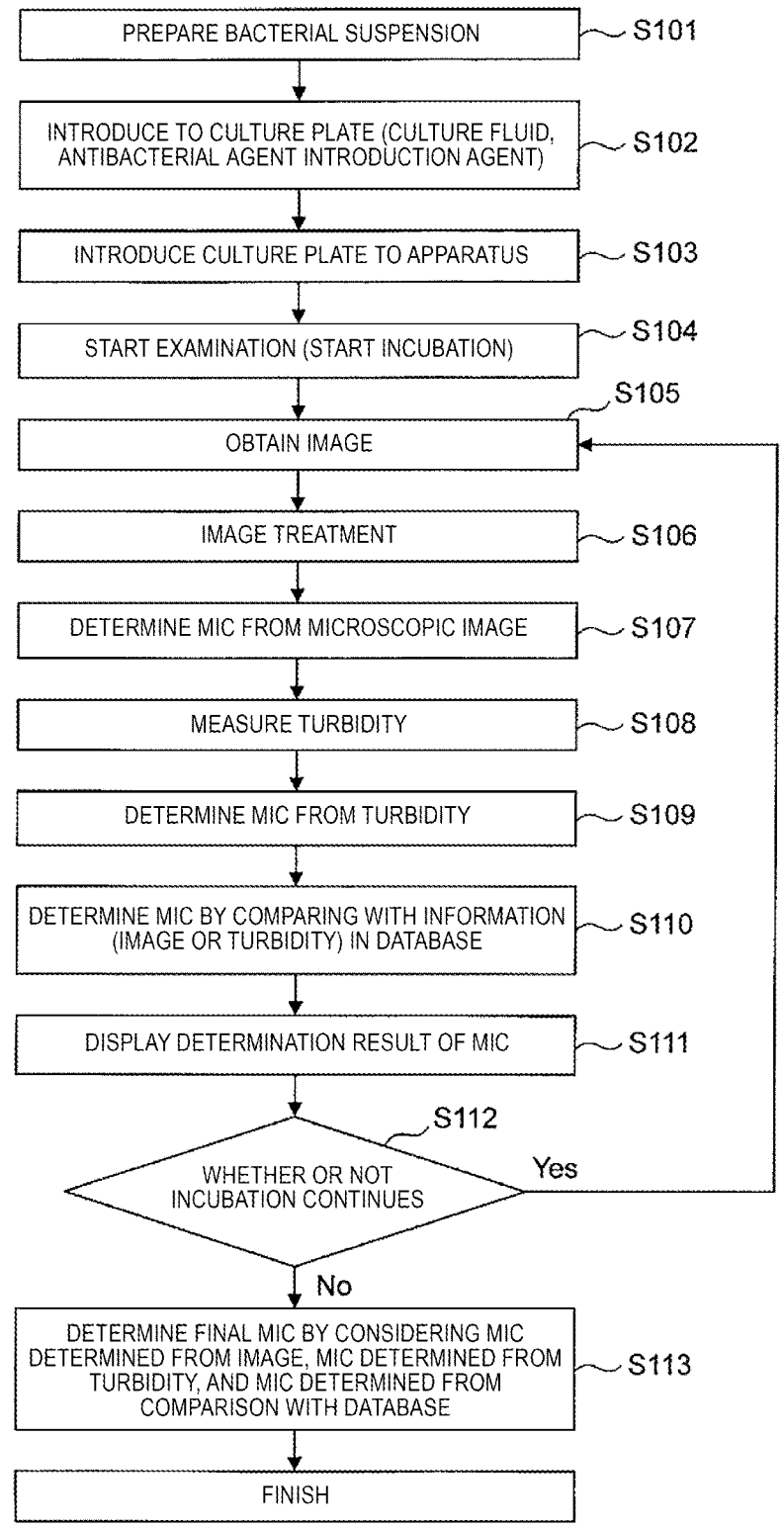

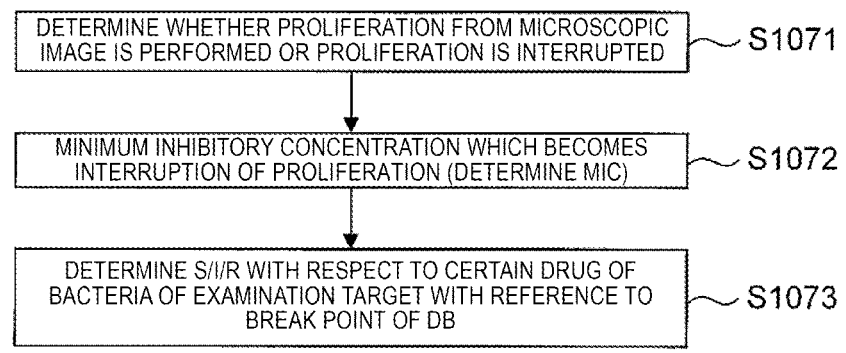
[Fig. 3B]

[Fig. 4]
*E. coli* (ATCC25922) + ABPC 0 μg/mL
(a) 0 min  (b) 180 min
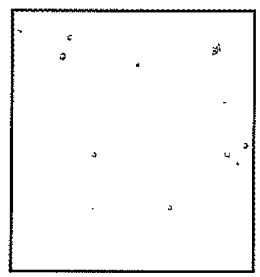 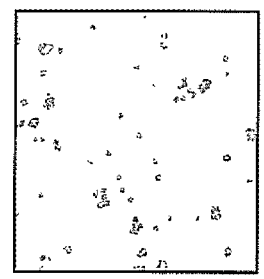
[Fig. 5]
*E. coli* (ATCC25922) + ABPC 2 μg/mL
(a) 0 min  (b) 180 min
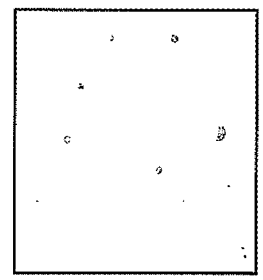 
[Fig. 6]
*E. coli* (ATCC25922) + ABPC 16 μg/mL
(a) 0 min  (b) 180 min
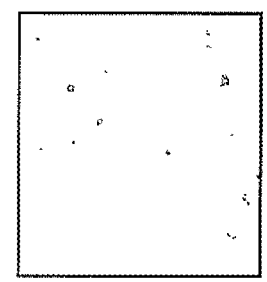 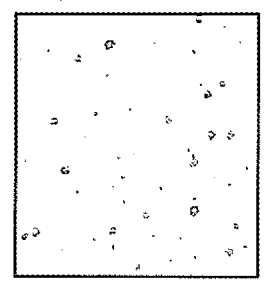

[Fig. 7]
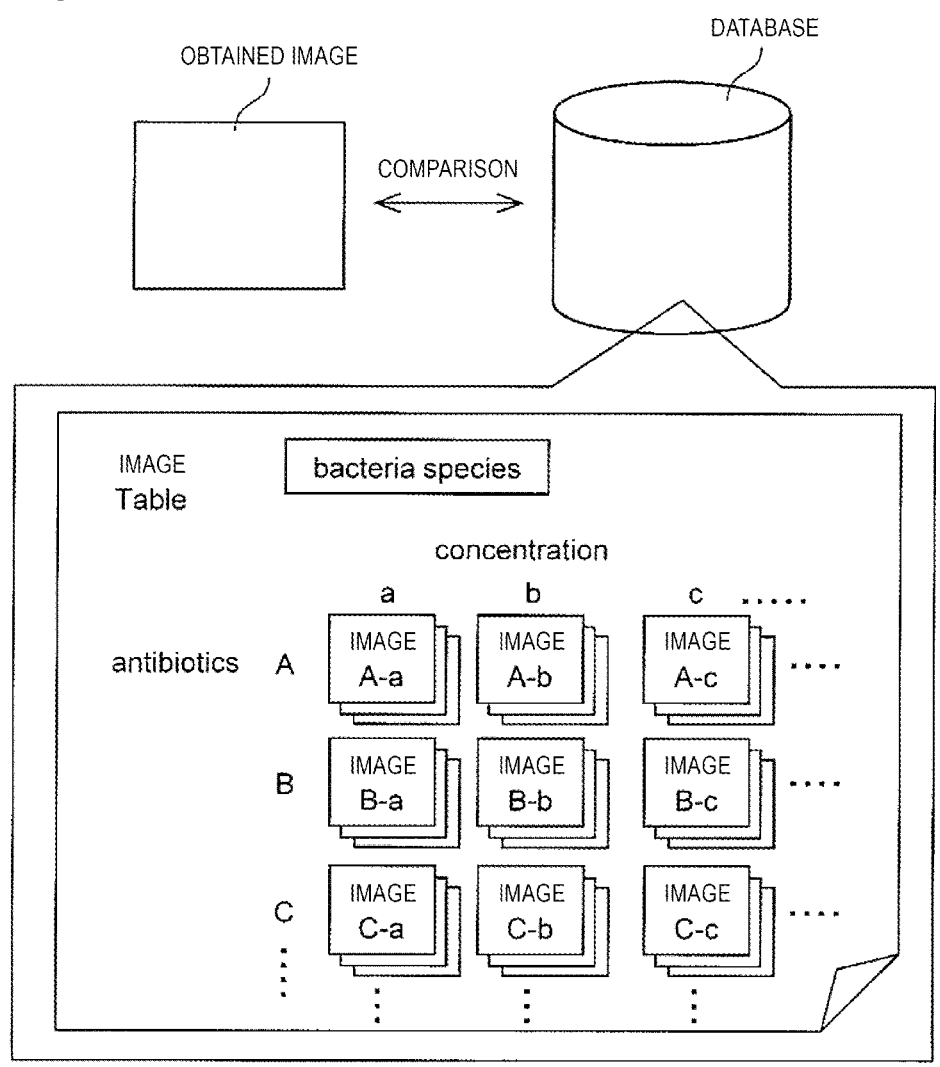

[Fig. 8]
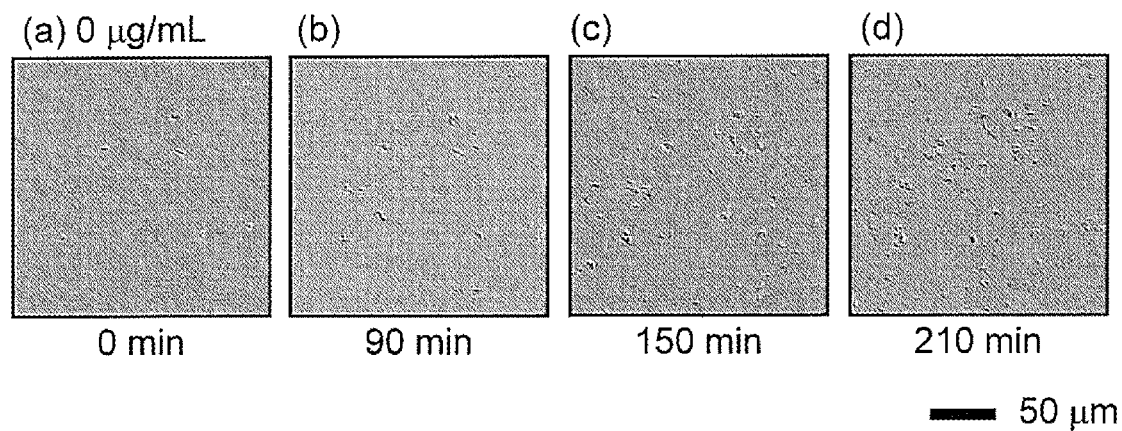
[Fig. 9]
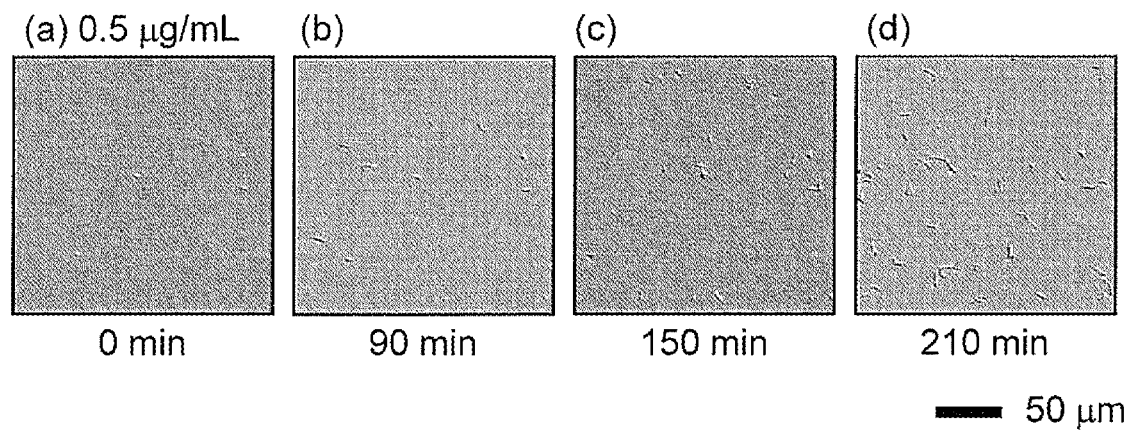

[Fig. 10]
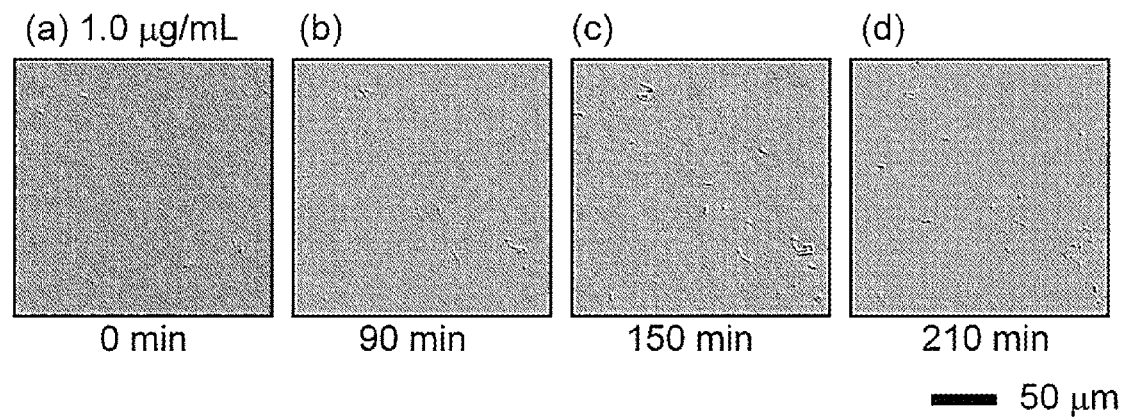
(a) 1.0 μg/mL  0 min  (b) 90 min  (c) 150 min  (d) 210 min  50 μm
[Fig. 11]
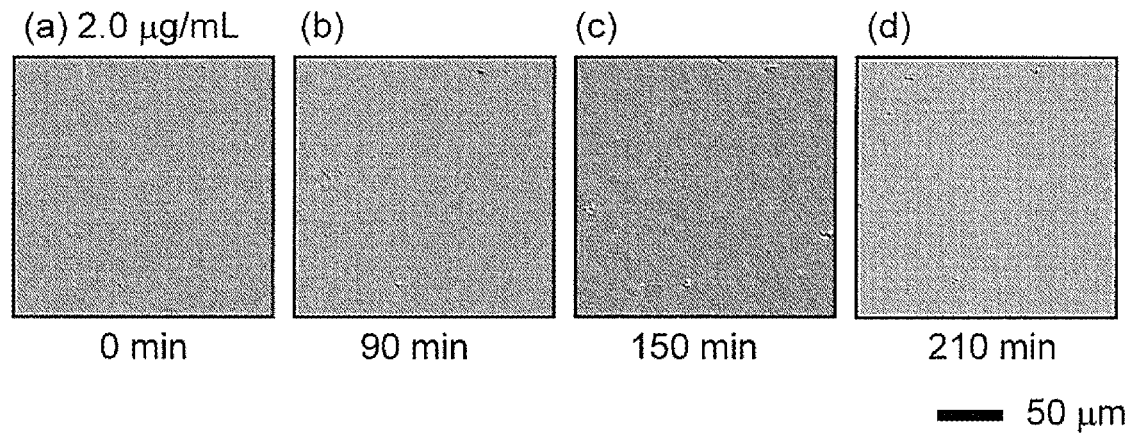
(a) 2.0 μg/mL  0 min  (b) 90 min  (c) 150 min  (d) 210 min  50 μm

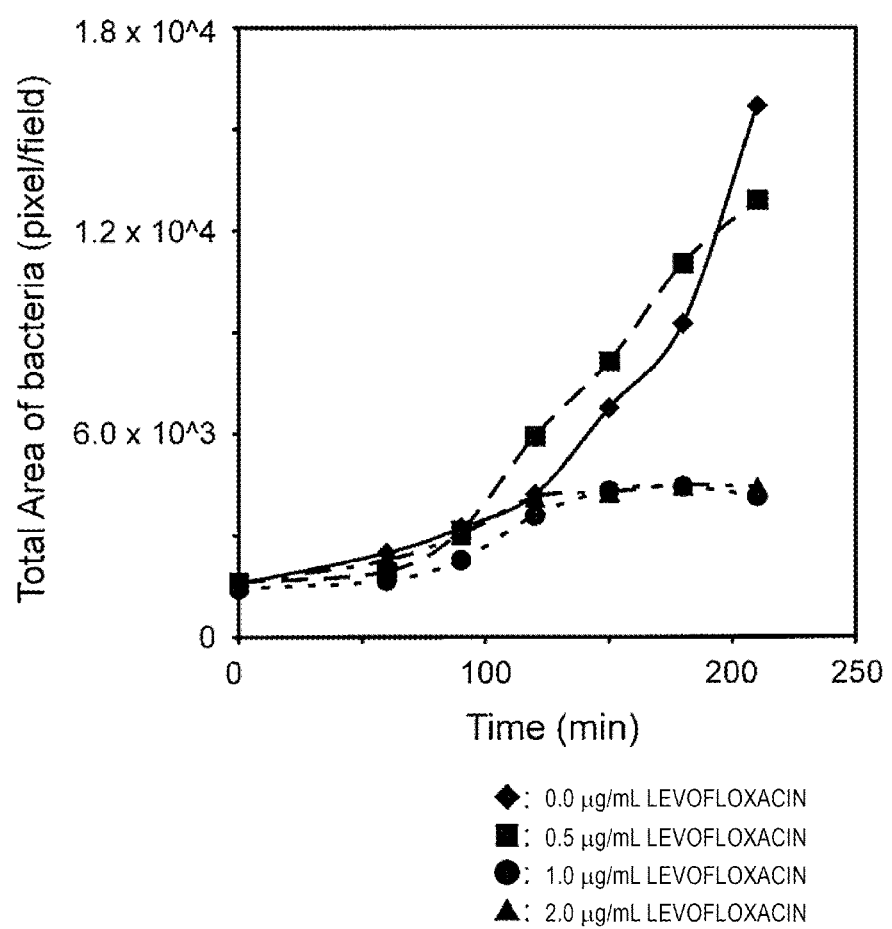
[Fig. 12]

[Fig. 13]

Result of antibiotic susceptibility test

| Time (min)<br>LVFX conc. | 60 | 90 | 120 | 150 | 180 | 210 |
|---|---|---|---|---|---|---|
| 0.0 g/μmL | W | W | W | G | G | G |
| 0.5 μg/mL | W | W | G | G | G | G |
| 1.0 μg/mL | W | W | W | I | I | I |
| 2.0 μg/mL | W | W | W | I | I | I |

W: Waiting
G: Growth
I: Inhibit
U: Unclear

[Fig. 14]

Result of antibiotic susceptibility test

| Time (min)<br>Antibiotic | 60 | 90 | 120 | 150 | 180 | 16 hrs |
|---|---|---|---|---|---|---|
| ABPC | W | W | R | R | R | R |
| CEZ | W | W | W | R | R | R |
| GM | W | W | W | S | S | S |
| LVFX | W | W | S | S | S | S |
| MEPM | W | S | S | S | S | S |
| VCM | W | W | W | I | I | I |

W: Wait
U: Unclear
S: Sensitive
I: Intermediate
R: Resistant

[Fig. 15]
(a)
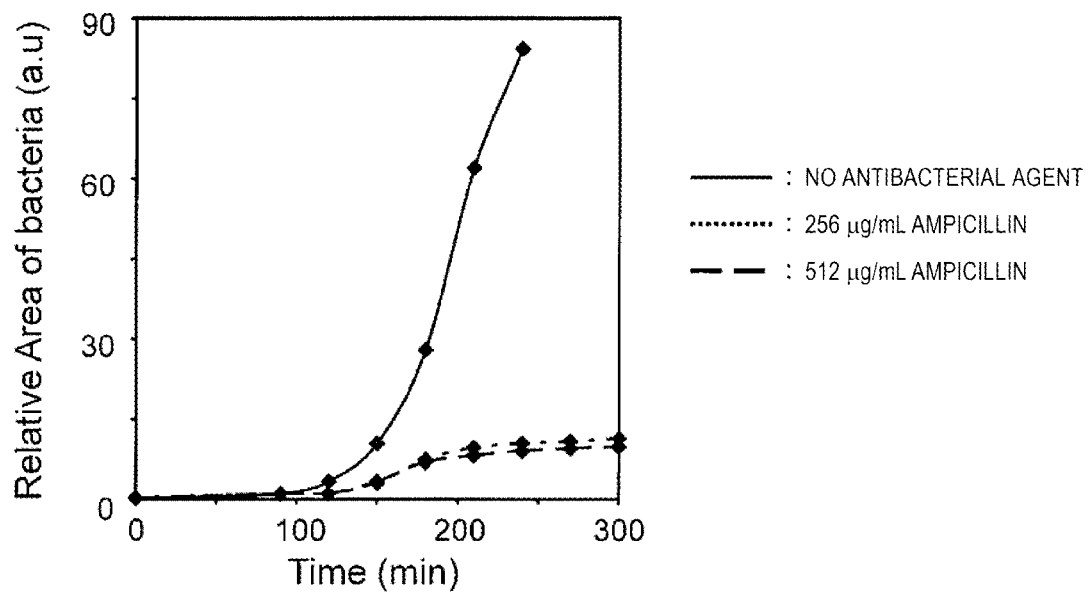
(b)
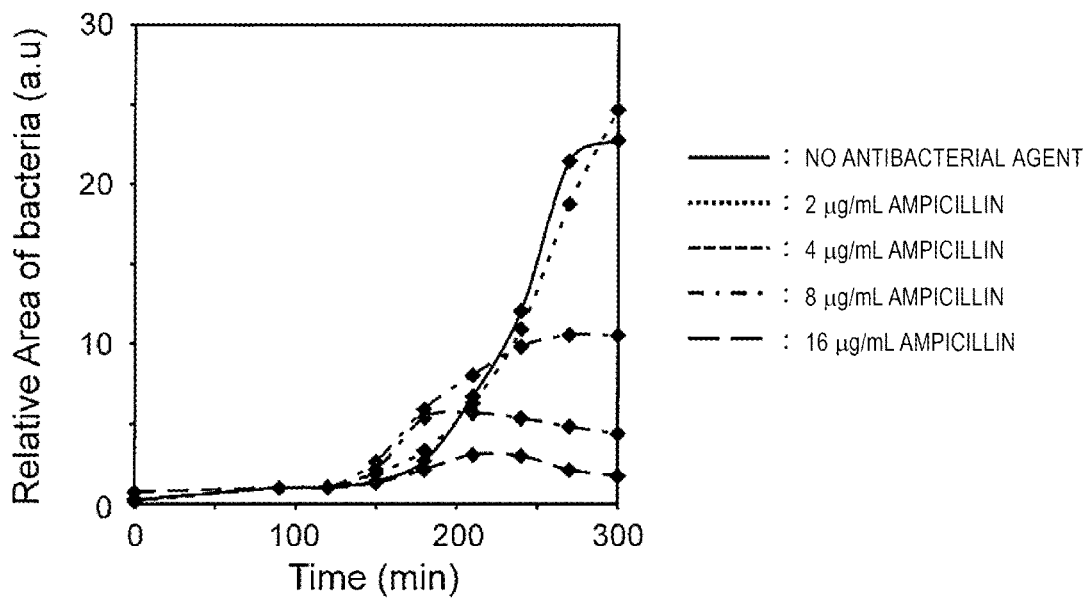

[Fig. 16]

(a) Result of antibiotic susceptibility test

| Time (min) ABPC conc. | 60 | 90 | 120 | 150 | 180 | 210 |
|---|---|---|---|---|---|---|
| 0.0 μg/mL | W | W | G | G | G | G |
| ......... | ... | ... | ... | ... | ... | ... |
| 256 μg/mL | W | W | W | W | G | G |
| 512 μg/mL | W | W | W | W | G | G |

W: Waiting
G: Growth
I: Inhibit
U: Unclear (b) Result of antibiotic susceptibility test

| Time (min) ABPC conc. | 60 | 90 | 120 | 150 | 180 | 210 |
|---|---|---|---|---|---|---|
| 0.0 μg/mL | W | W | W | W | G | G |
| 2 μg/mL | W | W | W | W | G | G |
| 4 μg/mL | W | W | W | G | G | G |
| 8 μg/mL | W | W | W | U | I | I |
| ......... | ... | ... | ... | ... | ... | ... |
| 32 μg/mL | W | W | W | W | U | I |

W: Waiting
G: Growth
I: Inhibit
U: Unclear

[Fig. 17]

(a)     Result of antibiotic susceptibility test

| Antibiotic \ Time (min) | 60 | 90 | 120 | 150 | 180 | 210 |
|---|---|---|---|---|---|---|
| ABPC | W | W | W | W | R | R |

(b)     Result of antibiotic susceptibility test

| Antibiotic \ Time (min) | 60 | 90 | 120 | 150 | 180 | 210 |
|---|---|---|---|---|---|---|
| ABPC | W | W | W | W | S | S |

W: Wait
U: Unclear
S: Sensitive
I: Intermediate
R: Resistant

[Fig. 18]
(a)
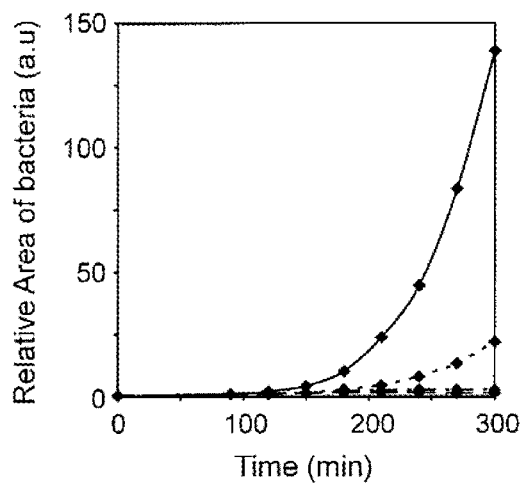
(b)
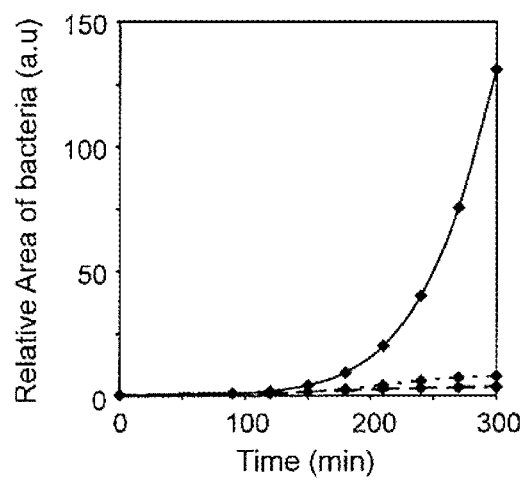
(c)
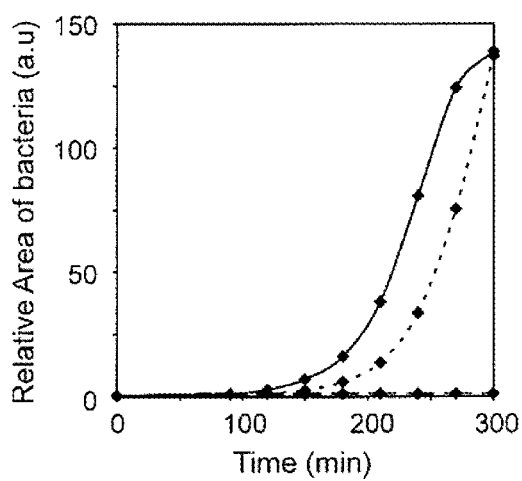
(d)
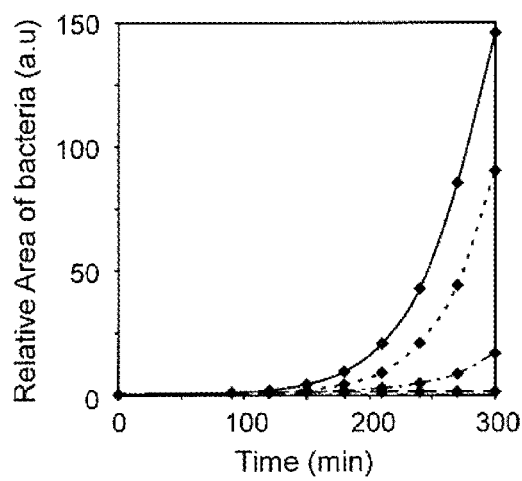

[Fig. 19]

(a) Result of antibiotic susceptibility test

| Time (min) | 90 | 120 | 150 | 180 | 210 | 240 |
|---|---|---|---|---|---|---|
| ABPC conc. 0.0 mg/mL | W | W | U | G | G | G |
| 0.125 mg/mL | W | W | W | U | U | G |
| 0.25 mg/mL | W | W | W | I | I | I |
| 0.5 mg/mL | W | W | W | I | I | I |
| VCM conc. 0.0 mg/mL | W | W | U | G | G | G |
| 0.25 mg/mL | W | W | W | U | G | G |
| 0.5 mg/mL | W | W | W | I | I | I |
| 1.0 mg/mL | W | W | W | I | I | I |

W: Waiting
G: Growth
I: Inhibit
U: Unclear (b) Result of antibiotic susceptibility test

| Time (min) | 90 | 120 | 150 | 180 | 210 | 240 |
|---|---|---|---|---|---|---|
| ABPC conc. 0.0 mg/mL | W | W | U | G | G | G |
| 0.125 mg/mL | W | W | W | I | I | I |
| 0.25 mg/mL | W | W | W | I | I | I |
| 0.5 mg/mL | W | W | W | I | I | I |
| VCM conc. 0.0 mg/mL | W | W | U | G | G | G |
| 0.25 mg/mL | W | W | W | U | G | G |
| 0.5 mg/mL | W | W | W | W | U | G |
| 1.0 mg/mL | W | W | W | I | I | I |

W: Waiting
G: Growth
I: Inhibit
U: Unclear

[Fig. 20]

(a) Result of antibiotic susceptibility test

| Antibiotic \ Time (min) | 60 | 90 | 120 | 150 | 180 | 210 | 240 | 16 hrs |
|---|---|---|---|---|---|---|---|---|
| ABPC | W | W | W | W | W | R | R | R |
| ...... | ... | ... | ... | ... | ... |  |  | ... |
| VCM | W | W | W | W | S | S | S | S |
| ...... | ... | ... | ... | ... | ... |  |  | ... |

W: Wait
U: Unclear
S: Sensitive
I: Intermediate
R: Resistant (b) Result of antibiotic susceptibility test

| Antibiotic \ Time (min) | 60 | 90 | 120 | 150 | 180 | 210 | 240 | 16 hrs |
|---|---|---|---|---|---|---|---|---|
| ABPC | W | W | W | W | W | S | S | S |
| ...... | ... | ... | ... | ... | ... |  |  | ... |
| VCM | W | W | W | W | W | W | I | I |
| ...... | ... | ... | ... | ... | ... |  |  | ... |

W: Wait
U: Unclear
S: Sensitive
I: Intermediate
R: Resistant

[Fig. 21]
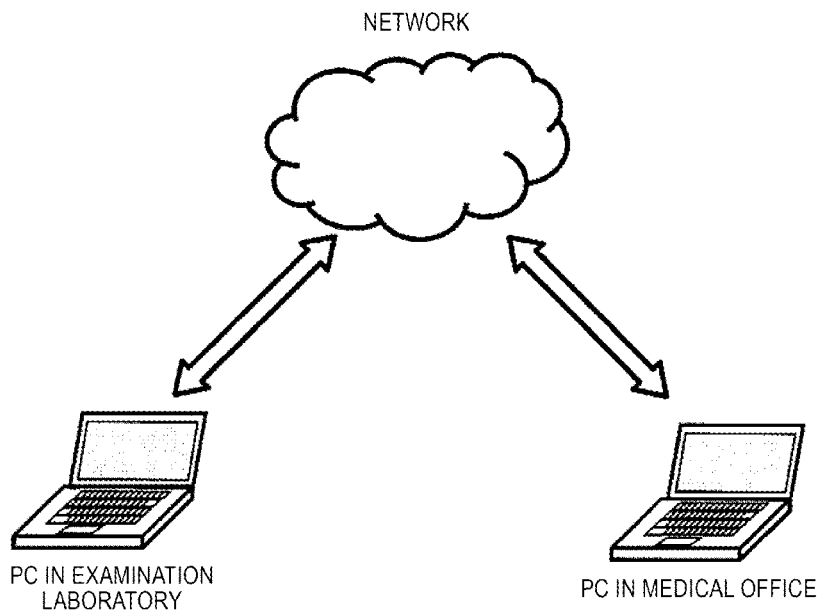
[Fig. 22]
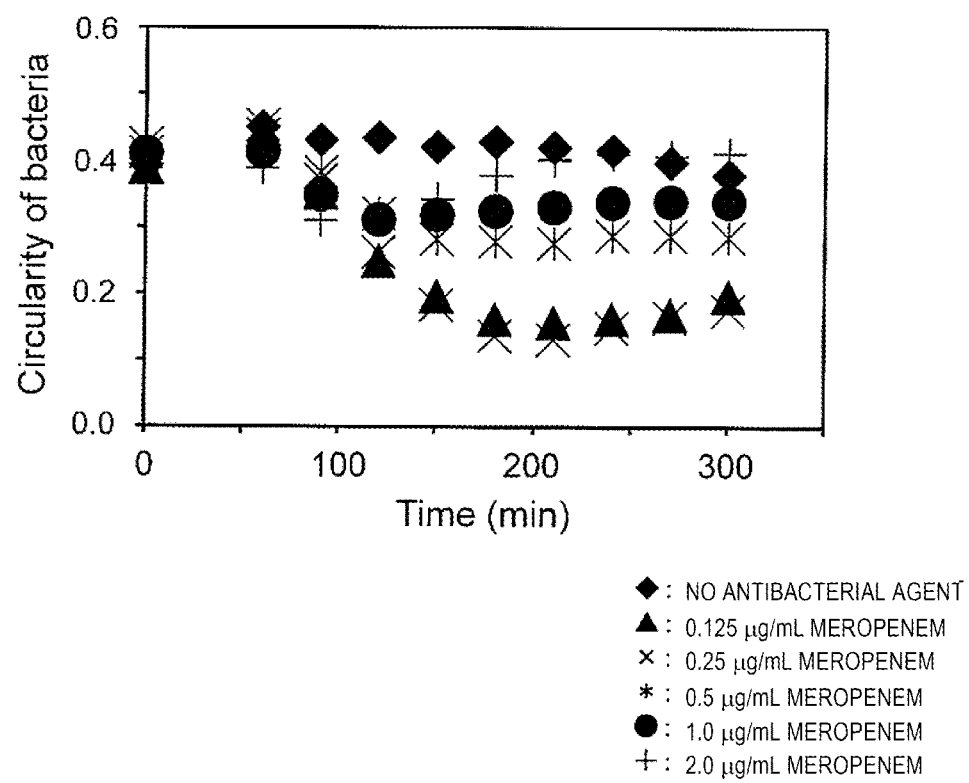

TEST DEVICE

TECHNICAL FIELD

The present invention relates to a testing instrument, and for example, relates to a testing instrument used in an antimicrobial susceptibility testing of bacteria or fungi.

BACKGROUND ART

Recently, antibiotics have been overused with respect to infectious disease patients, resulting in an increase of the proportion of drug-resistant bacteria. Accordingly, the number of instances of nosocomial infection tends to increase as well. However, the development of new antibiotics has decreased due to slimmer profit margins, and the number of types of the antibiotics approved by US FDA has been decreasing every year. Therefore, when an infectious disease occurs, it is vitally important to achieve early recovery of patients, to prevent the spread of nosocomial infection, and to suppress the emergence of drug-resistant bacteria by carrying out an identification testing and an antimicrobial susceptibility testing of the bacterial species of the causative bacteria thereof and using antibiotics properly.

In an examination method which is generally carried out in bacteriological examination laboratories in hospitals, a causative bacterium of an infectious disease is cultured and identification and antimicrobial susceptibility of the bacterial species are determined based on the presence or absence of proliferation thereof. First, a specimen such as blood, a throat swab, and sputum is collected from a patient. Then, isolation culture for obtaining the infection causative bacterium in a single colony is performed for overnight. A bacterial suspension is prepared from the single colony, and culture for examining identification culture or antimicrobial susceptibility is performed for overnight. The determination result of the antimicrobial susceptibility testing is obtained and appropriate medication is performed three days, for example, after the specimen is collected from the patient. An infection causative bacterium which has a slow proliferation rate and needs to be cultured for a long time requires more days.

As a testing instrument for achieving automation and energy-saving in isolation culture, a testing instrument which obtains an image of bacterial colonies in a culture dish and measures micro-organisms or cells, and the like have been developed (refer to PTL 1). In addition, an apparatus for simplifying the antimicrobial susceptibility testing has been sold (NPL 1). In the apparatuses, it is determined that bacteria are proliferated by the culturing and turbidity of a culture fluid increases.

Examples of a method which does not use the apparatus include a disk method based on a microdilution method and a Kirby-Bauer method (NPL 2).

CITATION LIST

Patent Literature

PTL 1: JP-A-2005-261260

Non-Patent Literature

NPL 1: Journal of Clinical Microbiology, 2000, vol. 38, No. 6, p. 2108-2111
NPL 2: Japanese Journal of Chemotherapy, 2002, vol. 50, No. 5, p. 259-265

SUMMARY OF INVENTION

Technical Problem

However, in a case of using an apparatus disclosed in PTL 1 or NPL 1, since a bacterium needs to proliferate until the turbidity become determinable, for example, in a case of bacteria such as *Pseudomonas aeruginosa* which slowly proliferates, the bacteria need to be cultured for at least eight hours or longer after a single colony is obtained.

In addition, in the method according to NPL 2, it also requires approximately 18 hours until obtaining the determination result after obtaining the single colony. Therefore, it is required to obtain the determination result quickly.

As described above, according to the methods of the related art, in order to perform a bacterial identification testing or an antimicrobial susceptibility testing, it is necessary to prepare a bacterial suspension from a single colony which is obtained after isolation culture and to perform culture for examining identification culture or antimicrobial susceptibility for overnight. As a result of being cultured, bacteria are grown under the conditions where bacteria proliferate, and turbidity of a culture fluid increases. In the methods of the related art, since it is determined whether or not the bacteria proliferate based on whether or not turbidity increases, there is a problem that it takes too much time for the determination. In addition, in the related art, every shape of the bacteria cannot be utilized for determination.

The invention has been made in consideration of the above-referenced circumstances, and there is provided a technology in which determination of bacterial identification or antimicrobial susceptibility can be promptly performed.

Solution to Problem

In order to solve the above-described problem, in the invention, there is provided a testing instrument which performs an identification testing or an antimicrobial susceptibility testing of bacteria or fungi. The testing instrument includes: a microscopic observation optical system which has a plurality of wells and performs microscopic observation at a plurality of points of time at which germs in a culture fluid containing antimicrobial or antifungal agents and the bacteria or fungi are set in advance in each of the wells; and a processor configured to display images obtained by the microscopic observation on a display screen. In addition, the processor is configured to generate influence determination information that shows influence given by the antimicrobial or antifungal agent to the bacteria or fungi with respect to plural types of antimicrobial agents and plural types of concentrations, based on the image, and displays the influence determination information in a time series.

Other features related to the invention will be clarified by the contents of this Description and the accompanying drawings. In addition, aspects of the invention will be achieved and realized in forms of the elements, combinations of various elements, the detailed description below, and the accompanying claims.

The contents in this Description are merely typical examples, and it is necessary to understand that claims and application examples of the invention are not limited by any means.

Advantageous Effects of Invention

According to the invention, determination of bacterial identification or antimicrobial susceptibility can be promptly performed.

BRIEF DESCRIPTION OF DRAWINGS

FIG. 1 is a view illustrating a schematic configuration example of a bacteriological testing instrument according to an embodiment of the invention.

FIG. 2 is a view illustrating a schematic configuration example of an optical system of the bacteriological testing instrument according to the embodiment of the invention.

FIG. 3A is a flowchart for describing a concept of examination processing in the bacteriological testing instrument according to the embodiment of the invention.

FIG. 3B a flowchart for describing detailed processing (step 107) of determining MIC from microscopic images.

FIG. 4 is a view illustrating Example 1 of an image (processed image) obtained by performing antimicrobial susceptibility testing in the bacteriological testing instrument according to the embodiment of the invention.

FIG. 5 is a view illustrating Example 2 of an image (processed image) obtained by performing antimicrobial susceptibility testing in the bacteriological testing instrument according to the embodiment of the invention.

FIG. 6 is a view illustrating Example 3 of an image (processed image) obtained by performing antimicrobial susceptibility testing in the bacteriological testing instrument according to the embodiment of the invention.

FIG. 7 is a view illustrating a concept of MIC determination processing according to comparison with database.

FIG. 8 is a view illustrating Example 1 of an image (raw image) obtained by performing the antimicrobial susceptibility testing, in Exemplary Embodiment 1 of the invention.

FIG. 9 is a view illustrating Example 2 of an image (raw image) obtained by performing the antimicrobial susceptibility testing, in Exemplary Embodiment 1 of the invention.

FIG. 10 is a view illustrating Example 3 of an image (raw image) obtained by performing the antimicrobial susceptibility testing, in Exemplary Embodiment 1 of the invention.

FIG. 11 is a view illustrating Example 4 of an image (raw image) obtained by performing the antimicrobial susceptibility testing, in Exemplary Embodiment 1 of the invention.

FIG. 12 is a graph (example) illustrating a state of proliferation of bacteria obtained by performing the antimicrobial susceptibility testing, in Exemplary Embodiment 1 of the invention.

FIG. 13 is a view illustrating a display example of proliferation determination result of bacteria obtained by performing the antimicrobial susceptibility testing, in Exemplary Embodiment 1 of the invention.

FIG. 14 is a view illustrating a display example of sensitivity determination result of bacteria obtained by performing the antimicrobial susceptibility testing, in Exemplary Embodiment 1 of the invention.

FIG. 15 is a graph (example) illustrating a state of proliferation of a plurality of bacteria obtained by performing antimicrobial susceptibility testing, in Exemplary Embodiment 2 of the invention.

FIG. 16 is a view illustrating a display example of proliferation determination result of the plurality of bacteria obtained by performing the antimicrobial susceptibility testing, in Exemplary Embodiment 2 of the invention.

FIG. 17 is a view illustrating a display example of sensitivity determination result of the plurality of bacteria obtained by performing the antimicrobial susceptibility testing, in Exemplary Embodiment 2 of the invention.

FIG. 18 is a graph (example) illustrating a state of proliferation of a plurality of bacteria obtained by performing antimicrobial susceptibility testing, in Exemplary Embodiment 3 of the invention.

FIG. 19 is a view illustrating a display example of proliferation determination result of the plurality of bacteria obtained by performing the antimicrobial susceptibility testing, in Exemplary Embodiment 3 of the invention.

FIG. 20 is a view illustrating a display example of sensitivity determination result of the plurality of bacteria obtained by performing the antimicrobial susceptibility testing, in Exemplary Embodiment 3 of the invention.

FIG. 21 is a view illustrating an example in which the sensitivity determination result of the bacteria obtained by performing the antimicrobial susceptibility testing via Internet is displayed, in Exemplary Embodiment 3 of the invention.

FIG. 22 is a graph (example) illustrating a state of time-dependent change of feature values of bacteria obtained by performing antimicrobial susceptibility testing, in Exemplary Embodiment 4 of the invention.

DESCRIPTION OF EMBODIMENT

Hereinafter, with reference to the accompanying drawings, an embodiment of the invention will be described. In the accompanying drawings, there are cases where the same number is applied to the elements having the same function. The accompanying drawings specifically illustrate an embodiment and implementation examples based on the principle of the invention. However, the accompanying drawings are provided so as to help others in understanding the invention and will never be used in order to limitedly interpret the invention.

The present embodiment is described in sufficient detail for those skilled in the art to carry out the invention. However, other types of implementation and forms can be applied. It is necessary to understand that changes in the configuration and the structure can be made and the elements can be variously replaced without departing from the scope and the gist of the technical idea of the invention. Thus, the following description shall not be interpreted in a manner of being limited thereto.

(1) Embodiment

Configuration of Bacteriological Testing Instrument

FIG. 1 is a view illustrating a schematic configuration of a bacteriological testing instrument according to the embodiment of the invention. The bacteriological testing instrument 1 includes a cover 11, a placement table 12, a microscopic observation optical system and a turbidity measurement optical system 13, a temperature controller 16, a gripper 17 for transporting a culture plate 18, and a drive control device 19 which controls movement and positioning of the gripper 17. In addition, the bacteriological testing instrument 1 includes a computer 20 for inputting information related to processing conditions and biological samples, information related to types and concentrations of antimicrobial agents, information related to patient specimens, and other various types of information. In addition, a configuration of the computer 20 is not illustrated, but similar to a general computer, the computer 20 is configured of a processor, a memory, a storage device, an input device (a keyboard, a mouse, a touch panel, or a microphone), an output device (a display, a printer, or a speaker), a storage device, or a communication device.

An examination performed by using the bacteriological testing instrument 1 is, for example, a antimicrobial susceptibility testing of bacteria or fungi. Here, the antimicrobial susceptibility testing denotes an examination in which bacteria or fungi is cultured in culture fluids respectively containing various types of antimicrobial or antifungal agents having predetermined concentrations and conditions of proliferation of the bacteria or the fungi are examined for antimicrobiotic resistance, or an examination determining the minimum inhibitory concentration (MIC) of bacteria or fungi. Target bacteria to be examined by using the bacteriological testing instrument 1 are not particularly limited. *Staphylococcus aureus, Enteroccoas faecalis, Streptococcus pneumoniae, E coli, Pseudomonas aeruginosa, Klebsiella pneumoniae*, and the like can be exemplified.

In addition, when an examination performed by using the bacteriological testing instrument 1, there are many cases where a bacterial suspension is prepared by using a single colony obtained from a clinical specimen through isolation culture. However, in a case where the possibility of contamination with respect to the clinical specimen is low and a single species of bacteria is included, without preparing the bacterial suspension, the specimen may be used with no change or may be used by being appropriately diluted.

Furthermore, when an examination is performed by using the bacteriological testing instrument 1, it is desirable that specimens are collected, are carried, and are subjected to isolation culture in accordance with a method recommended by the Clinical and Laboratory Standards Institute (CLSI, Wayne, Pa.). Preparation of antimicrobiotic agents and preparation of culture mediums are performed in a similar manner. However, the preparations are not limited thereto. In addition, it is also desirable that a culture temperature and a culture fluid to be used are adopted in a similar manner based on the method recommended by CLSI. However, the culture temperature and the culture fluid are not limited thereto.

In addition, when an examination is performed by using the bacteriological testing instrument 1, culture is performed by mixing a bacterial suspension prepared from a specimen with a culture fluid in the culture plate (for example, a culture plate which has 96 wells in total is used) 18. In order to perform the antimicrobial susceptibility testing, antimicrobial agents different from each other are set so as to be respectively contained in the culture fluids in each of the wells in particular concentrations. An order of the culturing is as follows. First, the bacterial suspension is introduced into the culture plate 18. Then, the bacterial suspension is in a state of being mixed with the culture fluid which is included in each of the wells, and the temperature controller 16 is set to a temperature of approximately 35° C. Furthermore, culture is performed by performing incubation such that the temperature of each of the wells in the culture plate 18 reaches the set temperature. Then, in the bacteriological testing instrument 1, while performing the incubation, the bacteria included in each of the wells can be monitored through the microscopic observation optical system. The microscopic observation may be performed for a set period of time from the start of the incubation till the end thereof by continuously monitoring the state of bacterial proliferation. In addition, the monitoring may be performed at the set time after setting appropriate time, and the monitoring result can be compared with the monitoring result when the incubation is started. In addition, similar to the bacteriological testing instrument in the related art, the turbidity of each of the wells may be measured through the turbidity measurement optical system while incubating the culture plate 18. The measured result may be compared with the monitored result of the microscopic observation optical system.

Configuration of Optical System

FIG. 2 is a view illustrating a configuration example of the microscopic observation optical system and the turbidity measurement optical system used in the bacteriological testing instrument 1 according to the embodiment of the invention. In FIG. 2, a culture plate 21 (the same as the culture plate 18) is irradiated with light from a light source 22. The light source may be a white light source or a light source such as an LED having a spectrum in a certain wavelength range. The light source 22 is adjusted by a filter 23 so as to be in a suitable wavelength range. When the microscopic observation is performed, there is no need to particularly limit the wavelength. However, when the measurement of the turbidity is performed, unnecessary wavelength ranges are cut by the filter 23 such that the culture plate 21 is irradiated with light having the wavelength in the vicinity of 600 nm.

In a case of the microscopic observation, the culture plate 21 is irradiated with light from the light source 22 via a dichroic mirror 24 and an objective lens 25. The scattered light from the culture plate 21 passes through the objective lens 25 and is measured by a CCD element 27, and a microscopic observation image is obtained.

In a case of the measurement of the turbidity, the light from the light source 22 passes through the objective lens 25, and the culture plate 21 is irradiated with light for the measurement of the turbidity through the dichroic mirror 24. The irradiation light is measured by a photodiode 26 installed above the culture plate 21. Meanwhile, the light which has passed through the dichroic mirror 24 is measured by the photodiode 26 installed on a side opposite to the light source 22. In accordance with the rule, the turbidity can be calculated based on the amount of light measured by the two photodiodes 26.

Contents of MIC Determination Processing

FIG. 3 is a flowchart for describing the MIC determination processing executed by the bacteriological testing instrument 1 according to the embodiment of the invention. FIG. 3A illustrates a concept of the processing in the bacteriological testing instrument 1, and FIG. 35 is a flowchart for describing step 107 in detail. In addition, the processing from steps 101 to 104 is performed by a "human". Therefore, the processing (processing executed by the computer (processor)) which is practically automatically executed is steps 105 to 113.

(FIG. 3A: Concept of Processing)

(i) Steps 101 to 104

A user prepares a bacterial suspension which is the specimen to be introduced into the apparatus (step 101), and the bacterial suspension is introduced into a culture plate (step 102). Thereafter, the culture plate is introduced into the bacteriological testing instrument (step 103). In addition, by using the computer 20 of the bacteriological testing instrument 1, the user instructs the testing instrument to start the examination by inputting necessary information such as information for the specimen or information for the antimicrobial agents, or by pushing a start button or the like (step 104). When receiving the instruction of the start of the examination, the culture plate introduced into the apparatus is incubated by the bacteriological testing instrument 1 to a temperature of approximately 35° C., and culture is performed.

(ii) Step 105

The processor of the computer 20 drives the microscopic optical system and obtains an image through microscopic observation of the wells in the culture plate at the time set in advance. In addition, the image obtaining may also be discretely performed at an interval determined in advance, or the image may also be obtained as an image for the processing at the time interval determined in advance through continuous observation.

(iii) Step 106

The processor carries out processing necessary for the obtained image. For example, as the image treatment, raw image data illustrated in FIGS. 8 to 11 is binarization-processed as illustrated in FIGS. 4 to 6, or is processed to grey scale image data. In addition, as another image treatment, processing of calculating the areas of the bacteria, the bacterial number, the circularity of the bacteria, the aspect ratio of the bacteria, and the perimeter length of the bacterium, based on the image data in FIGS. 4 and 6, is included.

(iv) Step 107

The processor attempts the MIC determination by using the image data obtained in step 106. The specific processing is as illustrated in FIG. 3B, and will be described later.

(v) Steps 108 to 109

The processor attempts the determination of the MIC from turbidity data by performing the turbidity measurement of each of the wells of the culture plate. In general, since it requires 18 hours or longer of time to perform the turbidity determination from the start of culture, it is not possible to perform the turbidity determination when 30 minutes or 1 hour is elapsed. Therefore, the MIC determination is not possible when 30 minutes or 1 hour has elapsed.

(vi) Step 110

The processor further attempts the determination of the MIC by comparing the information of the image or the information of turbidity (value) in the database, with the information of the image or the information of the turbidity which is obtained in the above-described step (refer to FIG. 7).

(vii) Step 111

The processor displays the determination result of the MIC or the like at this point of time. Specifically, the determination result (S/I/R determination, MIC determination, a time series graph, a microscopic image, or the like) obtained in step 107 is displayed.

(viii) Step 112

The processor determines whether or not the proliferation of the bacteria proceeds (whether or not the incubation is continuously performed) until the determination of the MIC can be finally confirmed. In a case where it is determined that the proliferation of the bacteria does not proceed (in a case of YES in step 112), the processor continues the incubation, and repeatedly performs the process from the image obtaining.

In a case where it is determined that the proliferation of the bacteria proceeds (in a case of NO in step 112), the processing moves to step 113. In other words, the MIC is determined with respect to the antimicrobial agent included in the culture plate, the processing with respect to the antimicrobial agent of which the MIC can be determined is completed, and in a case where it is determined that it is difficult to perform the determination with respect to the remaining antimicrobial agent, the processing moves to step 113.

(ix) Step 113

The processor determines final MIC considering the MIC determined from the image, the MIC determined from the turbidity, and the MIC determined from the comparison with the database, and the examination is completed. The process is automatically performed based on the condition set for each culture plate. In addition, a plurality of culture plates can be installed in the bacteriological testing instrument 1 at the same time, but a different condition may be changed for each of the culture plates, or the process may be performed under the same condition.

(FIG. 3B: Specific Step 107)

(i) Step 1071

The processor determines whether the bacteria proliferate or the proliferation is interrupted under the corresponding culture condition, based on the microscopic image to which the above-described necessary treatments are performed. The determination whether or not the proliferation is performed, is performed by comparing with the information obtained based on the images at different times in the same container. More specifically, based on the image after the treatment illustrated in FIGS. 4 to 6, for example, the areas of the bacteria are calculated, and it is determined whether or not the proliferation is performed by creating the graph as illustrated in FIG. 12.

(ii) Step 1072

The processor combines the information on whether or not the proliferation is performed under the culture condition with a combination of a certain concentration of the antimicrobial agent, and determines the minimum concentration of the antimicrobial agent (MIC, minimum inhibitory concentration) which becomes interruption of proliferation. Here, the MIC determination is performed with respect to all of the wells provided on the culture plate 21. For example, there are 96 wells on the culture plate 21, and various types of antimicrobial agents having different concentrations (for example, 0 μg/mL, 0.5 μg/mL, 1 μg/mL, 2.0 μg/mL, 4.0 μg/mL, 8.0 μg/mL, 16.0 μg/mL, . . . ) enter the wells. Therefore, the minimum concentration (MIC) of the antimicrobial agent which becomes interruption of proliferation can be ascertained.

(iii) Step 1073

The processor further determines whether the bacteria of the examination target is sensitive (S), resistant (R), and intermediate (I) with respect to the corresponding antimicrobial agent by comparing with a break point (a break point of Clinical and Laboratory Standards Institute (CLSI), a break point of Japanese Society of Chemotherapy, or a break point of EUCAST) which is stored as reference data. For example, in a case where the break point is 8 (at 8 μg/mL, the bacteria become extinct), 16 μg/mL is not clinically input even when the MIC determination is 16 (at 16 μg/mL, the bacteria become extinct), and in this case, it is determined that the bacteria is resistance (R).

Example of Microscopic Observation Image

FIGS. 4 to 6 are views illustrating an example of an image obtained by executing predetermined processing (for example, binarization processing) with respect to the image (raw image) obtained by a microscope.

During the microscopic observation, as a result of executing the predetermined processing with respect to raw image data, the image illustrated in FIGS. 4 to 6 is obtained. The obtained data is stored and held in the computer (control PC) 20, and is used in bacterial identification or determination of the MIC. Here, FIG. 4, for example, illustrates that images obtained by performing the microscopic observation with respect to the state where *E coli* (ATCC25922) in a Mueller-Hinton culture medium not containing ampicillin is cultured, are binarized. States after (a) zero minutes and (b) 180 minutes from the start of culture are respectively illustrated. Similarly, FIG. 5 illustrates a state where the *E coli* (ATCC25922) is cultured in a culture fluid containing ampicillin of 2 µg/mL, and FIG. 6 illustrates a state where the *E. coli* (ATCC25922) is cultured in a culture fluid containing ampicillin of 16 µg/mL, respectively, by performing the predetermined processing (binarization processing) through the microscopic observation. In FIGS. 4 to 6, black target subjects indicate the *E coli*.

For example, in FIG. 5(*b*), it is possible to confirm a state where the *E coli* (ATCC25922) in the culture fluid containing ampicillin of 2 µg/mL is elongated by an action of a β-lactamase antimicrobial agent.

Comparison with Images in Database

FIG. 7 is a view illustrating a concept of processing of comparing the obtained images (for example, images of FIGS. 4 to 6) with images accumulated in the database. In the antimicrobial susceptibility testing, culture is performed under the conditions in which the antimicrobial agents varied in type and concentration are applied to the bacteria which are the testing target, and the MIC is determined by testing whether or not the bacteria can proliferate. Here, the database stores the images of the bacteria in a case where culture is performed with particular types and concentrations of the antimicrobial agent for each species of the bacteria. Even though the species of the bacteria are the same as each other, when the strains thereof are different from each other, sensitivity with respect to a drug varies. Therefore, the MIC can be determined by performing comparison of the image which is similar to an image of the examination target obtained from a plurality of images stored in the database under the conditions of types and concentrations of the antimicrobial agent. In addition, regarding a certain antimicrobial agent, since the image in the database and the image of the examination target are compared in various concentrations, the MIC can be accurately performed. For example, as illustrated in FIG. 5(*b*), in a state where the bacteria are in an elongated state, the effect of the antimicrobial agent is achieved. However, eventually, it is confirmed that extinction of the bacteria has not achieved. Therefore, it can be ascertained that the MIC becomes higher than the concentration thereof.

In addition, instead of comparing the images with each other, identification or antimicrobial susceptibility of the bacteria may be determined by performing comparison of the bacterial numbers present in the image; the areas of the bacteria present in the image; and feature values such as the circularity, the aspect ratio, and the perimeter length of the bacterium extracted from the image. In this case, the feature values such as the average area, the circularity, the aspect ratio, and the perimeter length of the bacterium are extracted from the image stored in the database, and the feature values are extracted from an image obtained by the testing, thereby performing the MIC determination by comparing the feature values with each other. In a case where an enormous amount of the data is stored in the computer (control PC) 20, a form of performing comparison may be employed by storing an image database or various feature values of the bacteria in the server and having access thereto when the MIC determination is performed. The MIC can be determined by utilizing the information obtained by the microscopic observation. Therefore, the MIC can be determined not only from the result of the measurement of the turbidity, but also from the image, and thus, determination can be more accurately performed.

(2) Exemplary Embodiment

Exemplary Embodiment 1

FIGS. 8 to 11 are views illustrating the microscopic observation images (raw image data before the image treatment) of *Enterococcus faecalis* (ATCC29212). The obtained image data is stored and held in the control PC, and is used in the bacterial identification or the determination of the MIC. For example, FIG. 8 illustrates images obtained by imaging a state of the *Enterococcus faecalis* in the Mueller-Hinton culture medium not containing levofloxacin respectively after (a) zero minutes, (b) 90 minutes, (c) 150 minutes, and (d) 210 minutes from the start of culture. Similarly, FIG. 9 illustrates images of *Enterococcus faecalis* in the culture fluid containing levofloxacin of 0.5 µg/mL, FIG. 10 illustrates images thereof in the culture fluid containing 1.0 µg/mL, FIG. 11 illustrates images thereof in the culture fluid containing levofloxacin of 2.0 µg/mL, and the target subjects which appear to be white in FIGS. 8 to 11 are the *Enterococcus faecalis*.

In FIGS. 8 and 9, a state where *Enterococcus faecalis* proliferated and was divided in a chain state with the lapse of time after the start of culture could be observed. Meanwhile, in FIGS. 10 and 11, the *Enterococcus faecalis* was grown to a certain extent till the times of FIGS. 10(*c*) and 11(*c*) (after 150 minutes), but a state where the *Enterococcus faecalis* is hardly grown thereafter can be observed. FIG. 12 illustrates a graph that shows time-dependent change of the areas of the bacteria observed in the image. When there is no antimicrobial agent to be plotted by a "rhomboidal (diamond) shape" in the graph of FIG. 12, the areas of the bacteria in the *Enterococcus faecalis* under the condition where the concentration of levofloxacin to be plotted by a "square shape" is 0.5 µg/mL increase as time elapses. Meanwhile, in the graph of FIG. 12, an increase in areas of the bacteria in the *Enterococcus faecalis* to a certain degree till the time after 150 minutes under the condition where the concentration of levofloxacin to be plotted by a "circular shape" is 1.0 µg/mL, and under the condition where the concentration of levofloxacin to be plotted by a "triangular shape" is 2.0 µg/mL, is observed. However, the areas of the bacteria remain to be constant thereafter. In this manner, from the graph of FIG. 12, it is possible to determine whether or not the *Enterococcus faecalis* proliferates under each of the culture conditions.

FIG. 13 illustrates a table summarizing the determination result from the graph of FIG. 12. Under the condition where the antimicrobial agent is not contained, it is difficult to determine whether or not the proliferation is performed for 120 minutes from the start of culture, Waiting is determined, and "W" is displayed. After this, since the areas of the bacteria increase after 150 minutes, Growth is determined, and "G" is displayed. Under the culture condition where levofloxacin of 0.5 µg/mL is included, it is difficult to determine whether or not the proliferation is performed for 90 minutes after the start of culture, Waiting is determined, and "W" is displayed. After this, since the areas of the bacteria increase after 120 minutes, Growth is determined, and "G" is displayed. Under the culture condition where levofloxacin of 1.0 µg/mL, is included and under the culture condition where levofloxacin of 2.0 µg/mL is included, it is difficult to determine whether or not the proliferation is performed for 120 minutes after the start of culture, Waiting is determined, and "W" is displayed. After this, the areas of the bacteria do not increase even after 150 minutes, but the areas of the bacteria increase under the condition that does not include the antimicrobial agent which is a comparison target, and thus, Inhibit is determined, and "I" is displayed. The proliferation determination result illustrated in FIG. 13 is updated in each measurement and it can be displayed that the information gradually increases. For example, after 90 minutes, only the determination results from the measurement results after 60 minutes and 90 minutes are displayed, but after 120 minutes are elapsed, it is displayed that G is determined under the culture condition where levofloxacin of 0.5 µg/mL is included, in addition to the information. Furthermore, information displayed every time when the number of times of measurement increases as time elapses, is added.

In each of the antimicrobial agents, with respect to the type of bacteria, break points for determining resistant (R), intermediate (I), and sensitive (S) by the MIC are determined. FIG. 14 illustrates a result of determining R, I, and S with respect to each of the antimicrobial agents by performing the determination illustrated in FIG. 13 for each antimicrobial agent at each measurement time and comparing the break points. FIG. 14 is a view summarizing which antimicrobial agent is effective and which antimicrobial agent is ineffective with respect to a certain bacterium. Summarization by representing sensitivity with respect to the antimicrobial agent by R, I, and S by summarizing the data of the same type of bacteria obtained by separating the table illustrated in FIG. 14 according to the same facility, with respect to the plurality of bacteria, is antibiogram. In other words, in the antibiogram, in a certain specific facility, a probability (I) that a specific type of bacteria shows R, I, and S with respect to the antimicrobial agent, is described. FIG. 14 is a table which is a base thereof. When performing the antimicrobial susceptibility testing according to the embodiment of the invention, the result (R, I, and S) of the sensitivity determination for each measurement time is obtained. Therefore, the data which is a base of the antibiogram of the related art is obtained in more detail. Furthermore, FIG. 14 is configured of data obtained by the sensitivity determination (R, I, and S) at various concentrations with respect to each of the antimicrobial agents, that is, FIG. 13. Therefore, it is possible to refer to the result with respect to each of the antimicrobial agents. In addition, FIG. 13 is determined from the graph illustrated in FIG. 12 created based on the observation result at each measurement time. Therefore, it is possible to refer to time series data of the areas of the bacteria under the culture condition of various antimicrobial agent concentrations. In this manner, since it is possible to more specifically refer to the data that is the base of the antibiogram, not only the type of the antimicrobial agent but also the information of the sensitivity with respect to the antimicrobial agent can be promptly and specifically obtained.

The field of levofloxacin of antimicrobial agent is hatched by grey in the table illustrated in FIG. 14. In this manner, the antimicrobial agent which is currently being administered is highlighted (emphasized), and it is also possible to easily determine whether or not the use of the antimicrobial agent which is being administered should be continued. In addition, as the emphasizing, in addition to the highlighting, the antimicrobial agent may be displayed to be greater than other antimicrobial agents, may be displayed in a bold latter, or may be displayed by blinking.

In addition, the column of 16 hrs in the table of FIG. 14 is the result obtained by performing the determination of R, I, and S using the MIC determination according to the method of the related art, but the columns on the left side therefrom illustrate the result obtained by performing the determination of R, I, and S based on the measurement result at 60 to 180 minutes. In other words, in the related art, the determination of R, I, and S is performed after one night is elapsed from the start of culture, but according to the embodiment of the invention, it is possible to display the determination result of R, I, and S in each microscopic observation. In addition, it is possible to perform the determination based on the result measured thus for every time when the culture time is elapsed. Specifically, the information of the graph of FIG. 12 is added and displayed as the number of times of measurement increases, the determination result of FIG. 13 is added, and the result of FIG. 14 is also added and displayed.

As described above, it is possible to promptly display the determination result of the antimicrobial susceptibility according to the invention.

Exemplary Embodiment 2

FIG. 15 is a view illustrating an examination result of the E coli separated from different patients. Specifically, FIG. 15(a) illustrates time-depending change of the areas of bacteria in a case where the E coli separated from a patient A is cultured under the condition where ampicillin is included. In addition, FIG. 15(b) illustrates time-depending change of the E coli in a case where the E coli separated from a patient B is cultured under the condition where ampicillin is included. Both of FIGS. 15(a) and 15(b) standardize the areas of the bacteria by the areas of the bacteria when the culture is started.

In FIG. 15(a), compared to a case where the antimicrobial agent is not included, the area slightly increases even in a case of ampicillin of 512 µg/mL. Meanwhile, in FIG. 15(b), the increase tends to be stopped in a case of ampicillin of 4 µg/mL, and when the concentration of ampicillin is 8 µg/mL or greater, it can be ascertained that the bacteria are damaged due to the action of the ampicillin and the area tends to decrease.

FIG. 16 is a view illustrating the proliferation determination result (MIC determination result) of the E coli separated from each of the patients A and B. Any of the E. coli separated from the patient A illustrated in FIG. 16(a) is determined to proliferate. Meanwhile, in a case of the E coli separated from the patient B illustrated in FIG. 16(b), it is determined that the proliferation is interrupted after 180 minutes from the start of culture when the concentration of ampicillin is 8 µg/mL or greater. From the result, it is determined that the strains of the E coli separated from the patients A and B are different from each other. In the related art, the determination result of the antimicrobial susceptibility is obtained on the next day of the start of culture, but according to the invention, it is possible to perform the proliferation determination of the bacteria by interpreting the change in areas of the bacteria every time when performing the microscopic observation, and to promptly perform the determination of the strains of the bacteria.

In addition, FIG. 17 is a view illustrating the result (result of comparison with the break points) obtained by performing the sensitivity determination of the E coli separated from each of the patients A and B. With respect to the *E coli* separated from the patient A illustrated in FIG. 17(*a*), ampicillin durability is determined. Meanwhile, ampicillin sensitivity is determined in a case of the *E coli* separated from the patient B illustrated in FIG. 17(*b*).

Exemplary Embodiment 3

FIG. 18 is a view illustrating an examination result of *Staphylococcus aureus* separated from different patients. Specifically, FIGS. 18(*a*) and 18(*c*) illustrate time-dependent change of the areas of the bacteria in a case where the *Staphylococcus aureus* separated from the patient A is cultured under the condition where ampicillin or vancomycin is included. In addition, FIGS. 18(*b*) and 18(*d*) illustrate time-dependent change of the *E coli* in a case where the *Staphylococcus aureus* separated from the patient B is cultured under the condition where ampicillin or vancomycin is included. In FIGS. 18(*a*) to 18(*d*), the area of the bacteria is standardized by the area of the bacteria at the start of culture.

In FIG. 18(*a*), compared to a case where the antimicrobial agent is not included, the area slightly increases even in a case of ampicillin of 0.125 µg/mL, and proliferation of ampicillin is interrupted when the concentration of ampicillin is 0.25 µg/mL or greater. Meanwhile, in FIG. 18(*b*), the proliferation is substantially interrupted when the concentration of ampicillin is 0.125 µg/mL. In addition, in FIG. 18(*c*), when the antimicrobial agent is not included, in a case where the concentration of vancomycin is 0.25 µg/mL, the proliferation is confirmed, but in FIG. 18(*d*), the proliferation is recognized until the concentration of vancomycin reaches 0.5 µg/mL. In other words, it is determined that the *Staphylococcus aureus* separated from the patient A and the *Staphylococcus aureus* separated from the patient B have different MICs with respect to the ampicillin and vancomycin. Since the data illustrated in FIG. 18 is a result interpreted from the image obtained within 300 minutes from the start of culture, it can be ascertained that it is possible to more promptly recognize the strains of the bacteria compared to the method of the related art.

FIG. 19 is a view illustrating the proliferation determination result (MIC determination result) with respect to the *Staphylococcus aureus* separated from each of the patients A and B. With respect to the *Staphylococcus aureus* separated from the patient A illustrated in FIG. 19(*a*), it is determined that the proliferation is performed until the concentration of ampicillin reaches 0.125 µg/mL, and it is determined that the proliferation is interrupted when the concentration of ampicillin is 0.25 µg/mL or greater. In addition, it is determined that the proliferation is performed when the concentration of vancomycin is 0.25 µg/mL, and it is determined that the proliferation is interrupted when the concentration of vancomycin is 0.5 µg/mL or greater. Meanwhile, with respect to the *Staphylococcus aureus* separated from the patient B illustrated in FIG. 19(*b*), it is determined that the proliferation is interrupted when the concentration of ampicillin is 0.125 µg/mL or greater, it is determined that the proliferation is performed until the concentration of vancomycin reaches 0.5 µg/mL, and it is determined that the proliferation is interrupted when the concentration of vancomycin is 1.0 µg/mL or greater. From the result, it can be assumed that the *Staphylococcus aureus* separated from the patients A and B have different strains.

FIG. 20 is a view illustrating the result (result of comparison with the break points) obtained by performing a antimicrobial susceptibility testing with respect to the *Staphylococcus aureus* separated from each of the patients A and B. With respect to the *Staphylococcus aureus* separated from the patient A illustrated in FIG. 20(*a*), the resistance of ampicillin and the sensitivity of vancomycin are determined. Meanwhile, in the *Staphylococcus aureus* separated from the patient B illustrated in FIG. 20(*b*), the susceptibility of ampicillin and vancomycin is determined as Intermediate. In the related art, the determination of antimicrobial susceptibility is obtained on the next day of the start of culture. However, according to the invention, it is possible to perform the proliferation determination of the bacteria by interpreting the change of the areas of the bacteria every time when the microscopic observation is performed, and to promptly perform the determination of the sensitivity or resistance of the bacteria with respect to the antimicrobial, by using the proliferation determination of the bacteria at the concentrations of each of the antimicrobial agents.

As described above, by using the invention, for example, it is possible to promptly specify a route of nosocomial infection.

In addition, as illustrated in FIG. 21, at the point of time when the antimicrobial susceptibility result is obtained, by sending the result to a PC installed in a medical office via a network from a PC installed in an examination laboratory, a prompt response, for example, a change of antimicrobial agent or a change of a treating method, becomes possible.

Exemplary Embodiment 4

FIG. 22 is a view (graph) illustrating a result obtained by antimicrobial susceptibility testing with respect to meropenem of *Pseudomonas aeruginosa*. The graph acquires the circularity of the *Pseudomonas aeruginosa* in the image measured through the microscopic observation, and illustrates the time-dependent chance thereof. The plurality of *Pseudomonas aeruginosa* are observed in one image, but the circularity of each of the *Pseudomonas aeruginosa* is acquired, and the value obtained by calculating an average value of the bacteria in the image is plotted. In addition, the circularity is a value calculated by $4\pi \times (area)/(perimeter\ length)\textasciicircum 2$. When the bacteria have a completely circular shape, $4\pi \times \pi r\textasciicircum 2/(2\pi r)\textasciicircum 2=1$ is satisfied, and when the bacteria is deviated from a completely circular shape, the perimeter length increases, and thus, the circularity value decreases.

In the graph, in a case where there is no the antimicrobial agent to be plotted by a "rhomboidal (diamond) shape", the circularity of the *Pseudomonas aeruginosa* was hardly changed from the start of culture. However, when the concentration of meropenem to be plotted by a "triangular shape" in the graph is 0.125 µg/mL, in a case where the concentration of meropenem to be plotted by x is 0.25 µg/mL, the circularity starts to decrease after 90 minutes from the start of culture, and the *Pseudomonas aeruginosa* is elongated by the effect of the antimicrobial agent. When the concentration of meropenem to be plotted by * in the graph is 0.5 µg/mL, and when the concentration of meropenem to be plotted by a "circular shape" is 1.0 µg/mL, in a case where the concentration of meropenem to be plotted by + is 2.0 µg/mL, the circularity slightly decreases, and the circularity does not decrease so much after 20 minutes when BR>P. From the result, when the concentration of meropenem of which the circularity continues to decrease is 0.125 µg/mL and 0.25 µg/mL, the bacteria are elongated by the effect of the antimicrobial agent, but it is determined that the *Pseudomonas aeruginosa* has not become extinct yet. In addition, when the concentration of meropenem of which the decrease in circularity is stopped is 0.5 µg/mL, or greater, it is determined that the *Pseudomonas aeruginosa* becomes extinct. In a case where the bacteria are not extinct, the shape of the bacteria changes. However, since the bacteria become extinct at a higher concentration of antimicrobial agent, the circularity does not change. In other words, the circularity decreases once in accordance with the concentration of antimicrobial agent, and the circularity does not decrease at a higher concentration of antimicrobial agent, but the concentration can be estimated as MBC. The exemplary embodiment is an example in which the time-dependent change of the circularity of the bacteria is plotted instead of plotting the time-dependent change of the areas of the bacteria. However, in this manner, by plotting the time-dependent change of the feature values that become an index for indicating a degree of proliferation or growth of the bacteria in addition to the bacterial numbers or the areas of the bacteria, not only the minimum inhibitory concentration (MIC) of the bacteria but also the minimum bactericidal concentration (MBC) can be determined.

(3) Conclusion (i) In the antimicrobial susceptibility testing according to the invention, based on the image obtained by the microscopic observation, the influence determination information that shows influence given by the antimicrobial agent to the bacteria or fungi is generated with respect to the plural types of antimicrobial agents and the plural types of concentrations, and the influence determination information is displayed in a time series. According to this, it is possible to accelerate the selection of the treating method with respect to the patient, and to perform prompt and appropriate drug administration. In other words, in the invention, it is determined whether or not the bacteria proliferate by performing the microscopic observation with respect to the culture fluid for the bacterial identification culture or the antimicrobial susceptibility examination. Specifically, an testing instrument having a temperature adjusting function including: a light source for performing the microscopic observation of each of the wells in the culture plate for the bacterial identification culture or the antimicrobial susceptibility testing, a mirror, an objective lens, and a CCD for obtaining an image; a light source for performing measurement of absorbance of each of the wells in the culture plate, a mirror, and a photodiode; and an XYZ stage for changing the position of the culture plate in order to observe or measure each of the wells, is used. Here, the light source or the mirror for the microscopic observation may be the same as the light source or the mirror for the measurement of absorbance, or may be separately installed. The turbidity (absorbance in the vicinity of the wavelength of 600 nm) can be measured by installing a suitable bandpass filter between the light source and the mirror. The microscopic observation in white light can be performed by switching the bandpass filter with a different filter. In addition, a mirror may be installed in front of the CCD for obtaining the microscopic observation image, or the photodiode for measuring absorbance, and the mirror may be switched when performing measurement thereof. The culture plate is installed on the XYZ stage, culture is performed while the temperature is controlled to be approximately 35° C., the XYZ stage is operated at the set time, and the state of each of the wells in the culture plate is observed. Regarding controlling of the XYZ stage, switching of the bandpass filter, switching of the mirror, setting of the temperature controller, and the like, controlling is performed by setting the conditions using the control PC set in the testing instrument. In addition, the control PC also sets the timing to perform observation of the wells in the culture plate or the timing to perform measurement of absorbance and records the result thereof. In the testing instrument, while performing the culture, the shape or the number of bacteria in the wells is measured by the microscopic observation. The measurement result is interpreted by the PC, the time-dependent change of the shape, the number, or the area of the bacteria in the wells is made in a graph and is determined, and accordingly, it is determined whether or not the bacteria proliferate in each of the wells for each measurement. In addition, from the plurality of measurement results, it is predicted whether or not the bacteria of the corresponding well proliferate at the next time. In a case where the determination is difficult, the determination at the corresponding time is retained. By displaying the results on the screen, it is possible to perform the determination whether or not the bacteria proliferate at each measurement time. With respect to a certain bacterium, by comparing the results under the culture condition where the concentrations are different with respect to the antimicrobial agent, it is possible to determine the minimum inhibitory concentration (MIC) of the bacteria of the examination target. The data of the break points is held as the reference data, and by comparing the MIC, it is possible to determine and display the antimicrobial susceptibility (sensitive (S), Resistant (R), or Intermediate (I)) of the bacteria. Accordingly, it is possible to provide the prompt result to the user.

According to the invention, as described above, it is possible to perform the microscopic observation of bacteria in each of the wells in the culture plate and to perform the measurement of the turbidity of the culture fluid in each of the wells. The bacteriological testing instrument in the related art monitors the proliferation of bacteria by measuring the turbidity of the culture fluid. However, it takes approximately 5 to 6 hours from the start of culture for the turbidity of the culture fluid to start increasing in accordance with the proliferation of the bacteria. In addition, in the antimicrobial susceptibility testing, the culture fluid and the quantity of bacteria are defined, and it is not easy to reduce the time of examination by performing the measurement of absorbance. Generally, it is because the time until the bacteria are divided and reach the concentration in which the turbidity of the culture fluid increases is determined due to the division speed of the bacteria, and the speed thereof does not drastically change under normal culture conditions.

However, the growth of the bacteria can be monitored by Performing the microscopic observation using an objective lens of approximately twenty magnifications, so that it is possible to determine whether or not each of the bacteria is grown. Accordingly, when the phase shifts from an induction phase (lag phase) to a logarithmic phase (log phase), it is possible to determine whether or not the bacteria is grown. Generally, the proliferation profile of bacteria shifts from the induction phase to the logarithmic phase within 30 minutes to 3 hours. Therefore, it is possible to determine whether the bacteria proliferate faster than the determination performed based on the turbidity.

Furthermore, by displaying the determination result on the screen, it is possible to provide the information of resistance to antibiotics every time when the microscopic observation is finished. The number of times of microscopic observation also increases when the culture time is elapsed, the plurality of determination results are provided, and it is possible to gradually improve the accuracy of the determination result. It is possible to determine the proliferation of the bacteria at the plurality of concentrations with respect to a certain antimicrobial agent to determine MIC, and to promptly determine the antimicrobial susceptibility of the bacteria by comparing with the break points held as the reference data. As a result, it is possible to accelerate the selection of the treating method with respect to the patient, and to perform prompt and appropriate drug administration.

Furthermore, in the invention, the result of the antimicrobial susceptibility testing is displayed at each time set in advance, and the results of the antimicrobial susceptibility determination with respect to the plurality of bacteria or fungi are displayed in parallel. According to this, it is possible to help determination whether the strains of the bacteria are the same or are different from each other, or to help specification of the route of nosocomial infection.

(ii) The invention can also be realized by a program code of software which realizes the function of the embodiment. In this case, a storage medium in which the program code is recorded is provided in a system or an apparatus, and a computer (otherwise, a CPU or an MPU) of the system or the apparatus reads out the program code stored in the storage medium. In this case, the program code itself which is read out from the storage medium realizes the above-described function of the embodiment, and the program code itself and the storage medium storing the program code are configured to be the invention. As the storage medium for supplying such a program code, for example, a flexible disk, a CD-ROM, a DVD-ROM, a hard disk, an optical disk, a magneto-optic disk, a CD-R, a magnetic tape, a non-volatile memory card, and a ROM are used.

In addition, based on the instruction of the program code, an operating system (OS) driven in the computer, or the like may perform a portion or the entirety of the actual processing, and the above-described function of the embodiment may be realized through the processing. Moreover, the program code read out from the storage medium may be written in a memory in the computer. Thereafter, based on the instruction of the program code thereof, the CPU or the like of the computer may perform a portion of the entirety of the actual processing, and above-described function of the embodiment may be realized through the processing.

Moreover, the program code of the software which realizes the function of the embodiment may be delivered via a network. Accordingly, the program code may be stored in storage means such as the hard disk or the memory of the system or the apparatus; or the storage medium such as a CD-RW and a CD-R. Thus, when in use, the computer (otherwise, the CPU or the MPU) of the system or the apparatus may read out and execute the program code stored in the storage means or the storage medium.

Last, the process and the technique described herein are not essentially related to any particular apparatus, and it is necessary to understand that the process and the technique can be implemented by any suitable combination of the components. Moreover, various types of general-purpose devices can be used in accordance with the instructed description herein. In order to execute the above-described steps of the method, a dedicated apparatus may be established. In addition, various types of invention can be formed by appropriately combining multiple configuration elements disclosed in the embodiment. For example, some configuration elements may be deleted from the overall configuration elements indicated in the embodiment. Moreover, the configuration elements in the embodiments different from each other may be appropriately combined together. In the invention, description has been given regarding the specified examples for the explanation in all viewpoints, not for the limitation. Those skilled in the art can know that there are many suitable combinations of hardware, software, and firmware to carry out the invention. For example, the above-referenced software may be implemented by a wide-range program or a script language such as an assembler, C/C++, perl, Shell, PHP, and Java (registered trademark).

Moreover, in the above-described embodiment, the control lines or the information lines considered to be necessary in the description are indicated. All the control lines or the information lines in a product are not necessarily indicated. All the configurations may be connected to each other.

REFERENCE SIGNS LIST

1 BACTERIOLOGICAL TESTING INSTRUMENT
11 COVER
12 PLACEMENT TABLE
13 MICROSCOPIC OBSERVATION OPTICAL SYSTEM AND A TURBIDITY MEASUREMENT OPTICAL SYSTEM
16 TEMPERATURE CONTROLLER
17 GRIPPER
18, 21 CULTURE PLATE
19 DRIVE CONTROL DEVICE
20 PC (COMPUTER)
22 LIGHT SOURCE
23 FILTER
24 MIRROR (DICHROIC MIRROR)
25 OBJECTIVE LENS
26 PHOTODIODE
27 CCD ELEMENT

The invention claimed is:

1. An testing instrument which performs an identification testing or an antimicrobial susceptibility testing of bacteria or fungi, the testing instrument comprising:
   a microplate having a plurality of wells, wherein the microplate holds in wells germs in a culture fluid containing antimicrobial agents and the bacteria or fungi;
   an optical system that includes:
      a light source,
      a dichroic mirror that reflects light from the light source onto the microplate via an objective lens,
      a filter located between the light source and the dichroic mirror, wherein the filter selectively permits all wavelengths of light from the light source to pass to the dichroic mirror when microscopic observations are performed and permits only light from the light source having a first wavelength to pass to the dichroic mirror when measurements of turbidity are performed,
      a first photodiode that receives the light reflected by the dichroic mirror that has passed through the microplate,
      a second photodiode that receives light that passes through the dichroic mirror without being reflected to the microplate, and
      a CCD element that forms a microscopic image from light scattered by microplate via the objective lens;
   a processor communicatively coupled to the optical system, wherein the processor is configured to:
      obtain the microscopic image, by controlling the filter to permit all wavelengths of light from the light source to pass to the dichroic mirror and subsequently receiving the microscopic image from the CCD element,
      calculate turbidity of the culture fluid held in each well of the microplate, perform predetermined image processing on the microscopic image to form image data, calculate an image processing result based on the image data, generate influence determination information based the image processing result and the turbidity of the culture fluid held in each well of the microplate calculated, wherein the influence determination information indicates an influence of a target antimicrobial agent to the bacteria or fungi with respect to plural types of antimicrobial agents at one or more concentrations, and display the influence determination information in a time series on a display screen, and wherein the turbidity of the culture fluid held in each well of the microplate are calculated by:

controlling the filter to only pass the light from the light source having the first wavelength and comparing an amount of light received by the first photodiode and the second photodiode.

2. The testing instrument according to claim 1, wherein the processor is further configured to:

determine whether the bacteria or fungi proliferate or proliferation thereof is interrupted under a predetermined culture condition by comparing a plurality of images obtained the CCD element, specify a minimum inhibitory concentration by determining whether the bacteria or fungi proliferate or the proliferation thereof is interrupted under a plurality of concentration conditions, with respect to the target antimicrobial agent, perform antimicrobial susceptibility determination of the bacteria or fungi by comparing the minimum inhibitory concentration with a break point after specifying the minimum inhibitory concentration in the target antimicrobial agent, and display a result of the antimicrobial susceptibility determination on the display screen.

3. The testing instrument according to claim 2, wherein the processor is configured to highlight information on the antimicrobial agent designated in advance when displaying the result of the antimicrobial susceptibility determination.

4. The testing instrument according to claim 2, wherein the processor is further configured to:

display the result of the antimicrobial susceptibility determination on the display screen at each time set in advance, and display the result of the antimicrobial susceptibility determination regarding a plurality of bacteria or fungi in parallel.

5. The testing instrument according to claim 2, wherein the processor is further configured to:

perform the antimicrobial susceptibility determination for different patients, and display the result of the antimicrobial susceptibility determination for the different patients on the display screen at each time set in advance to be capable of distinguishing strains of the bacteria or fungi by comparison.

6. The testing instrument according to claim 1, wherein the processor is further configured to:

determine whether or not the bacteria or fungi proliferate or the proliferation thereof is interrupted at each time set in advance under each of a plurality of concentration conditions of the target antimicrobial agent, and display a determination result on the display screen based on whether or not the bacteria or fungi proliferate or the proliferation thereof is interrupted.

7. The testing instrument according to claim 1, wherein the processor is further configured to:

generate a graph which plots a time series change of areas of the bacteria or fungi by acquiring the areas of the bacteria or fungi based on whether or not the bacteria or fungi proliferate at the time set in advance under each of a plurality of concentration conditions of the target antimicrobial agent, and displays the graph generated on the display screen.

8. The testing instrument according to claim 1, wherein the processor is configured to align and display images obtained by the CCD element under a target culture condition on the display screen in a time series.

9. The testing instrument according to claim 1, wherein the processor is further configured to:

align and display the microscopic image in accordance with a plurality of concentration conditions of the target antimicrobial agent.

10. The testing instrument according to claim 1, wherein the predetermined processing includes binarization and the image data includes grey scale image data.

11. The testing instrument according to claim 1, wherein the image processing result includes at least one of:

areas of the bacteria or fungi, a number of the bacteria or fungi, a circularity of the bacteria or fungi, an aspect ratio of the bacteria or fungi, and a perimeter length of the bacteria or fungi.

12. The testing instrument according to claim 1, wherein the first wavelength is 600 nm.

13. An testing instrument which is a bacteriological examination device that performs an identification testing or a antimicrobial susceptibility testing of bacteria or fungi, the testing instrument comprising:

a microplate having a plurality of wells, wherein the microplate holds in wells germs in a culture fluid containing antimicrobial agents and the bacteria or fungi;

an optical system that includes:

a light source, a dichroic mirror that reflects light from the light source onto the microplate via an objective lens, a filter located between the light source and the dichroic mirror, wherein the filter selectively permits all wavelengths of light from the light source to pass to the dichroic mirror when microscopic observations are performed and permits only light from the light source having a first wavelength to pass to the dichroic mirror when measurements of turbidity are performed, a first photodiode that receives the light reflected by the dichroic mirror that has passed through the microplate, a second photodiode that receives light that passes through the dichroic mirror without being reflected to the microplate, and a CCD element that forms a microscopic image from light scattered by microplate via the objective lens; and a processor communicatively coupled to the optical system, wherein the processor is configured to:

obtain the microscopic image, by controlling the filter to permit all wavelengths of light from the light source to pass to the dichroic mirror and subsequently receiving the microscopic image from the CCD element, calculate turbidity of the culture fluid held in each well of the microplate, perform predetermined processing on the microscopic image to generate image data, calculate at least one of feature values of the bacteria or fungi based on the image data and the turbidity of the culture fluid held in each well of the microplate calculated, wherein the at least one of the feature values includes a circularity, a perimeter length, and a number of the bacteria or fungi, and display the at least one feature values of the bacteria or fungi on a display screen, wherein the turbidity of the culture fluid held in each well of the microplate are calculated by:

controlling the filter to only pass the light from the light source having the first wavelength, and comparing an amount of light received by the first photodiode and the second photodiode.

14. The testing instrument according to claim 13, wherein the predetermined processing includes binarization and the image data includes grey scale image data.

15. The testing instrument according to claim 13, wherein the first wavelength is 600 nm.

* * * * *